(12) United States Patent
Ramsey

(10) Patent No.: US 7,560,099 B2
(45) Date of Patent: Jul. 14, 2009

(54) FINAL FINISH AFTERSHAVE

(76) Inventor: Donald D. Ramsey, 4311 Foxton Ct., Dayton, OH (US) 45414

( * ) Notice: Subject to any disclaimer, the term of this patent is extended or adjusted under 35 U.S.C. 154(b) by 0 days.

(21) Appl. No.: 11/619,030

(22) Filed: Jun. 25, 2007

(65) Prior Publication Data

US 2008/0317872 A1 Dec. 25, 2008

(51) Int. Cl.
*A61K 8/26* (2006.01)
*A61K 8/19* (2006.01)
*A61K 8/25* (2006.01)

(52) U.S. Cl. ................................ 424/70.1; 424/698

(58) Field of Classification Search ............... 424/70.1, 424/698
See application file for complete search history.

(56) References Cited

U.S. PATENT DOCUMENTS 4,478,853 A * 10/1984 Chaussee .................... 514/772

* cited by examiner

*Primary Examiner*—Johann R Richter
*Assistant Examiner*—Courtney Brown
(74) *Attorney, Agent, or Firm*—Dinsmore & Shohl LLP

(57) ABSTRACT

A fragrant, topical antiseptic, astringent mixture which eliminates the bumping caused by the use of a razor and/or a depilatory is provided. The aftershave composition includes aluminum potassium sulfate dodecahydrate and an aromatic oil in a 70% by volume solution of isopropyl alcohol.

2 Claims, No Drawings

FINAL FINISH AFTERSHAVE

BACKGROUND

The irritation experienced by many males resulting from shaving with a razor and/or a depilatory has been well documented. There are several causes, the most outstanding being the tendency of the clipped hair to curl and grow inward beneath the skin surface. The shave surface then bumps as the combined result of shaving irritation and clipped hairs which have not grown straight through the skin.

SUMMARY

The action of an astringent solution works to eliminate and prevent shaving irritation. The addition of aluminum potassium sulfate dodecahydrate to isopropyl alcohol causes the pore size of the shave surface to be reduced and gives the topical antiseptic needed to eliminate inflammation. The reduction of pore sizes denies the clipped hair the room to curl inward, therefore causing it to grow straight through the skin surface which, essentially, prepares it for clipping again.

DETAILED DESCRIPTION

The following proportions of each ingredient are used to make the after shave solution:

To 95 ml. of 70% by volume isopropyl alcohol is added 5 grams aluminum potassium sulfate dodecahydrate. The mixture is allowed to sit for 2 hours. The resulting solution is then filtered to recover 0.6 grams unreacted $AlK(SO_4)_2.12H_2O$.

To the resulting solution is added 5 ml. concentrated aromatic oil drop wise over a period of 30 minutes. The solution is stirred or shaken constantly during this addition.

The resulting solution is a fragrant, topical antiseptic, astringent mixture which eliminates the bumping caused by the use of a razor and/or a depilatory.

What is claimed is:

1. An after shave composition comprising, 4.4 grams of aluminum potassium sulfate dodecahydrate and 5 ml. of an aromatic oil in 95 ml. of 70% by volume isopropyl alcohol.

2. A method of reducing shaving irritation caused by a razor or a depilatory comprising applying an aftershave composition comprising aluminum potassium sulfate dodecahydrate and an aromatic oil in a 70% by volume solution of isopropyl alcohol to the skin after shaving.

* * * * *